(12) United States Patent
Gonzalez-Hernandez

(10) Patent No.: US 8,506,588 B2
(45) Date of Patent: Aug. 13, 2013

(54) SUTURE RETRIEVER-SHEATH DILATOR TOOL AND METHOD FOR USE THEREOF

(75) Inventor: Eduardo Gonzalez-Hernandez, Coconut Grove, FL (US)

(73) Assignee: Toby Orthopaedics, Inc., Coral Gables, FL (US)

( * ) Notice: Subject to any disclaimer, the term of this patent is extended or adjusted under 35 U.S.C. 154(b) by 622 days.

(21) Appl. No.: 12/586,055

(22) Filed: Sep. 16, 2009

(65) Prior Publication Data

US 2010/0137883 A1 Jun. 3, 2010

Related U.S. Application Data

(60) Provisional application No. 61/097,240, filed on Sep. 16, 2008.

(51) Int. Cl.
*A61B 17/02* (2006.01)
(52) U.S. Cl.
USPC .......................................... 606/190; 606/191
(58) Field of Classification Search
USPC ................. 606/108, 139–143, 148, 151–156, 606/191, 198, 222, 224, 228; 623/13.11–13.2, 623/1.23; 600/201, 210, 235; 604/264, 506
See application file for complete search history.

(56) References Cited

U.S. PATENT DOCUMENTS

| 3,620,218 A | 11/1971 | Schmitt et al. |
| 3,842,441 A | 10/1974 | Kaiser |
| 4,584,722 A | 4/1986 | Levy et al. |
| 4,733,850 A | 3/1988 | Thompson |
| 4,781,191 A | 11/1988 | Thompson |
| 5,431,153 A | 7/1995 | Lee |
| 5,531,232 A | 7/1996 | Hill |
| 5,651,790 A * | 7/1997 | Resnick et al. ............... 606/167 |
| 5,803,904 A | 9/1998 | Mehdizadeh |
| 5,893,861 A | 4/1999 | Yumoto |

(Continued)

FOREIGN PATENT DOCUMENTS

| EP | 1 757 231 A1 | 2/2007 |
| GB | 2 424 372 A | 9/2006 |

(Continued)

OTHER PUBLICATIONS

U.S. Appl. No. 12/807,962, filed Sep. 2010, Gonzalez-Hernandez.

(Continued)

*Primary Examiner* — Ryan Severson
*Assistant Examiner* — Rachel S Papeika
(74) *Attorney, Agent, or Firm* — Martin & Ferraro, LLP

(57) ABSTRACT

A tool serves to facilitate one or more of dilation of a flexor tendon sheath and corresponding pulleys, attachment of a severed flexor tendon thereto, passage of the severed flexor tendon through the flexor tendon sheath and the corresponding pulleys, and reattachment of the severed flexor tendon. The tool includes a tip portion, a shaft portion, and a handle portion. During use of the tool, the tip portion and at least a part of the shaft portion can be passed through the flexor tendon sheath, and the handle portion is can be used to control such passage. The tip portion and the shaft portion can be used to dilate the flexor tendon sheath. The severed flexor tendon can be attached to the tip portion, and the tool can be withdrawn from flexor tendon sheath to pass the severed flexor tendon to a repair site.

11 Claims, 6 Drawing Sheets

(56) References Cited

U.S. PATENT DOCUMENTS

| | | | |
|---|---|---|---|
| 5,897,591 | A | 4/1999 | Kobayashi |
| 6,033,361 | A | 3/2000 | Co et al. |
| 6,056,762 | A | 5/2000 | Nash et al. |
| 6,083,244 | A | 7/2000 | Lubbers et al. |
| 6,984,241 | B2 | 1/2006 | Lubbers et al. |
| 7,112,221 | B2 | 9/2006 | Harris |
| 7,144,424 | B2 | 12/2006 | Steenlage |
| 2005/0033338 | A1 | 2/2005 | Ferree |
| 2005/0159812 | A1 | 7/2005 | Dinger, III et al. |
| 2005/0203620 | A1 | 9/2005 | Steiner et al. |
| 2005/0228426 | A1 | 10/2005 | Campbell |
| 2005/0245958 | A1 | 11/2005 | Carlson et al. |
| 2006/0041270 | A1* | 2/2006 | Lenker et al. ............ 606/198 |
| 2007/0162022 | A1 | 7/2007 | Zhang et al. |
| 2007/0288043 | A1* | 12/2007 | Rehnke ............ 606/170 |
| 2008/0109021 | A1 | 5/2008 | Medoff |
| 2009/0048616 | A1 | 2/2009 | Gonzalez-Hernandez |
| 2011/0015656 | A1 | 1/2011 | Gonzalez-Hernandez |
| 2012/0071975 | A1 | 3/2012 | Gonzalez-Hernandez |
| 2012/0078283 | A1 | 3/2012 | Gonzalez-Hernandez |
| 2012/0083848 | A1 | 4/2012 | Gonzalez-Hernandez |

FOREIGN PATENT DOCUMENTS

| | | |
|---|---|---|
| JP | HEI 09-56720 | 9/1997 |
| JP | HEI 09-75362 | 9/1997 |
| WO | WO 2006/085090 A2 | 8/2006 |
| WO | WO 2008/017834 | 2/2008 |

OTHER PUBLICATIONS

U.S. Appl. No. 61/403,116, filed Sep. 2010, Gonzalez-Hernandez.

Biologically Oriented Prostheses (BIOPRO); Tendone!® product brochure; 2 pages.

Kamath, B. Jagannath, et al.; Technique Article; A Simple, Semirigid, and Surgeon-Friendly Tendon Retriever and Flexor Sheath Dilator; The Journal of Hand Surgery, vol. 32A, No. 2, Feb. 2007, pp. 269-273.

Sourmelis, S.G., et al.; Retrieval of the Retracted Flexor Tendon; Journal of Hand Surgery (British and European Volume), vol. 12-B, No. 1, Feb. 1987, pp. 109-111 and cover page.

Supplementary Partial European Search Report; Application No. EP08827278; mailed Jun. 30, 2011; 6 pages.

* cited by examiner

SUTURE RETRIEVER-SHEATH DILATOR TOOL AND METHOD FOR USE THEREOF

RELATED APPLICATIONS

This application claims the benefit of provisional Application No. 61/097,240, filed Sep. 16, 2008, which is incorporated herein by reference.

BACKGROUND OF THE INVENTION

1. Field of the Invention

The present invention is generally related to a tool and method for use thereof for facilitating repair of a severed tendon. More particularly, the present invention is related to a tool and method for use thereof for facilitating retrieval and reattachment of a severed flexor tendon. More specifically, the present invention relates to a tool and method for use thereof for facilitating dilation of a flexor tendon sheath and corresponding pulleys, attachment of a severed flexor tendon thereto, passage of the severed flexor tendon through the flexor tendon sheath and the corresponding pulleys, and reattachment of the severed flexor tendon.

2. Description of the Prior Art

Fingers in the hand are moved by flexor and extensor tendons arising from muscles in the forearm. The mechanism facilitating movement of the fingers using the flexor tendons includes three main components in each of the fingers: 1) the skeleton, including phalanges and corresponding articulations (or interphalangeal joints) between the phalanges; 2) a flexor tendon sheath; and 3) the flexor tendons themselves.

In each finger, two flexor tendons work to flex the proximal and distal interphalangeal joints, namely the flexor digitorum superficialis and the flexor digitorum profundis, respectively. Furthermore, the flexor tendon sheath holds the flexor tendons in close proximity to the phalanges of each finger to ensure that their pull produces immediate movement at the interphalangeal joints. In the absence of the flexor tendon sheaths, the flexor tendons simply "bow-string" and fail to produce the desired joint motion.

The flexor tendon sheath is highly specialized tissue that is anchored to bone and forms a very smooth but tight fibrous tunnel around the flexor tendons. With the flexor tendons surrounded by the flexor tendon sheath, there is a measurable hydrostatic pressure within the substance of the tendons. The flexor tendon sheath is not a uniform fibrous tunnel, but rather, is made of identifiable individual segments. The individual segments that make up the flexor tendon sheath are referred to as pulleys because of the mechanical role they play: i.e., holding the flexor tendons close to the phalanges; preventing "bow-stringing" of the flexor tendons; and ultimately translating pull of the flexor tendons into joint motion.

For decades, surgical repair of severed flexor tendons has proven challenging. When the flexor tendons of a finger are severed, the flexor tendons retract through the flexor tendon sheath. Thus, to facilitate repair thereof, the severed flexor tendons must be passed through the flexor tendon sheath to a repair site. However, the ends of the severed flexor tendons swell, and, in the absence of the flexor tendons, the flexor tendon sheath (including the corresponding pulleys) contracts. Accordingly, passing the severed flexor tendons through the flexor tendon sheath is difficult.

Therefore, there is a need for a tool and method for use thereof for facilitating retrieval and reattachment of a severed flexor tendon. Such a tool and method for use thereof should facilitate one or more of dilation of a flexor tendon sheath and corresponding pulleys, attachment of a severed flexor tendon thereto, passage of the severed flexor tendon through the flexor tendon sheath and the corresponding pulleys, and reattachment of the severed flexor tendon.

SUMMARY OF THE INVENTION

The present invention in one preferred embodiment contemplates a suture retriever-sheath dilator tool for use in surgery on a tendon of a patient including a distal end, a proximal end opposite the distal end, and a length between the distal and proximal ends, a shaft having a distal end, a proximal end opposite the distal end, and a length between the distal and proximal ends of the shaft, the shaft being configured to pass at least in part through a tendon sheath, the shaft having a first cross section transverse to the length of the shaft having a convex upper surface configured to contact an inner surface of the tendon sheath, the first cross section of the shaft having a concave lower surface opposite the upper surface configured to contact an outer surface of the tendon, the shaft having a thickness perpendicular to the length of the shaft and between the upper and lower surfaces, the shaft having a width perpendicular to the thickness and the length of the shaft, the shaft increasing in thickness from the distal end of the shaft to the proximal end of the shaft over at least a portion of the length of the shaft, a tip extending from the distal end of the shaft for insertion into and through the tendon sheath, the tip being configured to permit a suture in the tendon to be attached to the tip, and a handle extending from the proximal end of the shaft.

The present invention in a further preferred embodiment contemplates a suture retriever-sheath dilator tool for use in surgery on a tendon of a patient including a distal end, a proximal end opposite the distal end, and a length between the distal and proximal ends, a shaft having a distal end, a proximal end opposite the distal end, and a length between the distal and proximal ends of the shaft, the shaft being configured to pass at least in part through a tendon sheath, the shaft having a first cross section transverse to the length of the shaft having a convex upper surface configured to contact an inner surface of the tendon sheath, the cross section of the shaft having a lower surface opposite the upper surface configured to contact an outer surface of the tendon, the shaft having a thickness perpendicular to the length of the shaft and between the upper and lower surfaces, the shaft having a width perpendicular to the thickness and the length of the shaft, the shaft increasing in thickness and width from the distal end of the shaft to the proximal end of the shaft over at least a portion of the length of the shaft, a tip extending from the distal end of the shaft for insertion into and through the tendon sheath, the tip being configured to permit a suture in the tendon to be attached to the tip, and a handle extending from the proximal end of the shaft.

The present invention in a yet further preferred embodiment contemplates a suture retriever tool for use in surgery on a tendon of a patient including a distal end, a proximal end opposite the distal end, and a length between the distal and proximal ends, a shaft having a distal end, a proximal end opposite the distal end, and a length between the distal and proximal ends of the shaft, the shaft being configured to pass at least in part through a tendon sheath, the shaft having a first cross section transverse to the length of the shaft having a convex upper surface configured to contact an inner surface of the tendon sheath, the first cross section of the shaft having a concave lower surface opposite the upper surface configured to contact an outer surface of the tendon, the shaft having a thickness perpendicular to the length of the shaft and between the upper and lower surfaces, the shaft having a width perpendicular to the thickness and the length of the shaft, a tip extending from the distal end of the shaft for insertion into and through the tendon sheath, the tip being configured to permit a suture to be attached to the tip, and a handle extending from the proximal end of the shaft.

The present invention in another preferred embodiment contemplates a suture retriever-sheath dilator tool for use in surgery on a tendon of a patient including a distal end, a proximal end opposite the distal end, and a length between the distal and proximal ends, a shaft having a distal end, a proximal end opposite the distal end, and a length between the distal and proximal ends of the shaft, the shaft being configured to pass at least in part through a tendon sheath, the shaft having a first cross section transverse to the length of the shaft having a convex upper surface configured to contact an inner surface of the tendon sheath, the first cross section of the shaft having a lower surface opposite the upper surface configured to contact an outer surface of the tendon, the shaft having a thickness perpendicular to the length of the shaft and between the upper and lower surfaces, the shaft having a width perpendicular to the thickness and the length of the shaft, the shaft increasing in thickness from the distal end of the shaft to the proximal end of the shaft over at least a portion of the length of the shaft, the shaft being formed of an elastic flexible material, the shaft having a pre-insertion cross section along a portion of the length of the shaft that is configured to apply pressure to the inner surface of the tendon sheath when the tool is inserted into the sheath, the shaft having a first post-insertion cross section that is smaller than the pre-insertion cross section as a result of the pressure applied to the shaft by the sheath, the shaft having a second post-insertion cross section that is greater than the first post-insertion cross section as a result of the material of the shaft moving toward the shape of the pre-insertion cross section, each of the pre-insertion cross section and the first and second post-insertion cross sections being measured through the same plane perpendicular to the length of the shaft, the shaft having a second pre-insertion cross section along a portion of the length of the shaft that is configured to apply pressure to the inner surface of the tendon sheath when the tool is inserted into the sheath, the second pre-insertion cross section being between the first pre-insertion cross section and the handle, the shaft having another first post-insertion cross section that is smaller than the second pre-insertion cross section as a result of the pressure applied to the shaft by the sheath upon further insertion of the shaft into the sheath, the shaft having another second post-insertion cross section that is greater than the another first post-insertion cross section as a result of the material of the shaft moving toward the shape of the second pre-insertion cross section, each of the second pre-insertion cross section, the another first post-insertion cross section, and another second post-insertion cross section being measured through the same plane perpendicular to the length of the shaft, a tip extending from the distal end of the shaft for insertion into and through the tendon sheath, the tip being configured to permit a suture in the tendon to be attached to the tip, and a handle extending from the proximal end of the shaft.

The present invention in yet another preferred embodiment contemplates a suture retriever tool for use in surgery on a tendon of a patient including a distal end, a proximal end opposite the distal end, and a length between the distal and proximal ends, a shaft having a distal end, a proximal end opposite the distal end, and a length between the distal and proximal ends of the shaft, the shaft being flexible and configured to pass at least in part through a tendon sheath, the shaft having a first cross section transverse to the length of the shaft having a convex upper surface configured to contact an inner surface of the tendon sheath, the first cross section of the shaft having a concave lower surface opposite the upper surface configured to contact an outer surface of the tendon, the shaft having a thickness perpendicular to the length of the shaft and between the upper and lower surfaces, the shaft having a width perpendicular to the thickness and the length of the shaft, the convex upper surface having a radius and the concave lower surface having a radius, the radius of the lower surface being greater than the radius of the upper surface, a tip extending from the distal end of the shaft for insertion into and through the tendon sheath, the tip having a hole configured to permit a suture needle to pass therethrough, and a handle extending from the proximal end of the shaft, the handle having an upper surface that is at an obtuse angle to the upper surface of the shaft.

The present invention also contemplates a method for performing surgery on a tendon of a patient by providing a tool having a shaft having a distal end, a proximal end opposite the distal end, and a length between the distal and proximal ends of the shaft, the shaft being configured to pass at least in part through a tendon sheath, the shaft having a first cross section transverse to the length of the shaft having a convex upper surface configured to contact an upper surface of an interior surface of the tendon sheath, the first cross section of the shaft having a lower surface opposite the upper surface configured to contact one of a lower surface of the interior surface of the tendon sheath and an outer surface of the tendon, the shaft having a thickness perpendicular to the length of the shaft and between the upper and lower surfaces, the shaft having a width perpendicular to the thickness and the length of the shaft, the shaft increasing in thickness from said distal end of the shaft to said proximal end of the shaft over at least a portion of the length of the shaft, the shaft being formed of an elastic flexible material, the shaft having a first pre-insertion cross section along a portion of the length of the shaft that is configured to apply pressure to the inner surface of the tendon sheath when the tool is inserted into the sheath, inserting the distal end of the shaft of the tool into the tendon sheath so that at least a portion of the shaft applies radial pressure to the interior surface the tendon sheath, the shaft having a first post-insertion cross section that is smaller than the pre-insertion cross section as a result of the pressure applied to the shaft by the sheath, waiting a period of time for the material of the shaft to move toward the shape of the first pre-insertion cross section, the shaft having a second post-insertion cross section that is greater than the first post-insertion cross section as a result of the material of the shaft moving toward the shape of the pre-insertion cross section, each of the pre-insertion cross section and the first and second post-insertion cross sections being measured through the same plane perpendicular to the length of the shaft, and inserting the distal end of the shaft of the tool further into the tendon sheath so that a portion of the shaft having a larger cross section than the first pre-insertion cross section applies radial pressure to the interior surface of the tendon sheath to further dilate the tendon sheath.

It is understood that both the foregoing general description and the following detailed description are exemplary and exemplary only, and are not restrictive of the invention as claimed.

BRIEF DESCRIPTION OF THE DRAWINGS

The accompanying drawings, which are incorporated in and constitute a part of the specification, illustrate preferred embodiments of the invention. Together with the description, they serve to explain the objects, advantages and principles of the invention. In the drawings.

DETAILED DESCRIPTION OF THE PREFERRED EMBODIMENT

The following description is intended to be representative only and not limiting, and many variations can be anticipated according to these teachings. Reference will now be made in detail to the preferred embodiments of this invention, examples of which are illustrated in the accompanying drawings.

Figure 3:
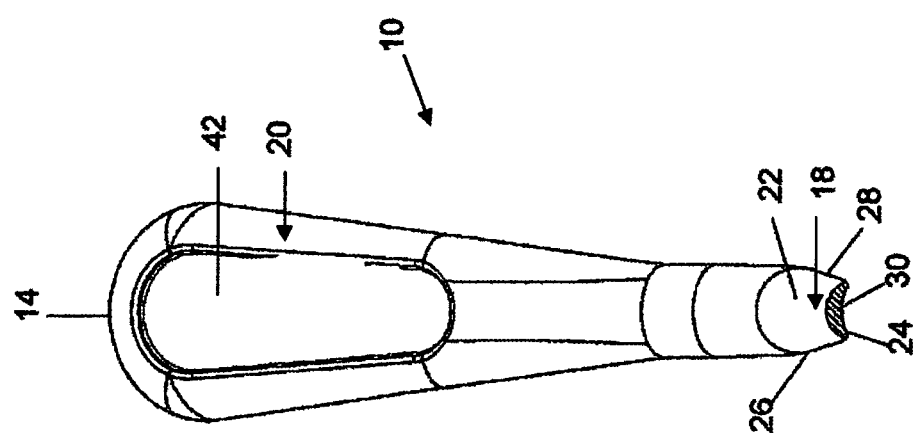
FIG. 3 is a front elevational partially cross-sectional view of the tool of FIG. 1, the cross-section being taken along Line 3-3 of FIG. 2.
Figure 4:
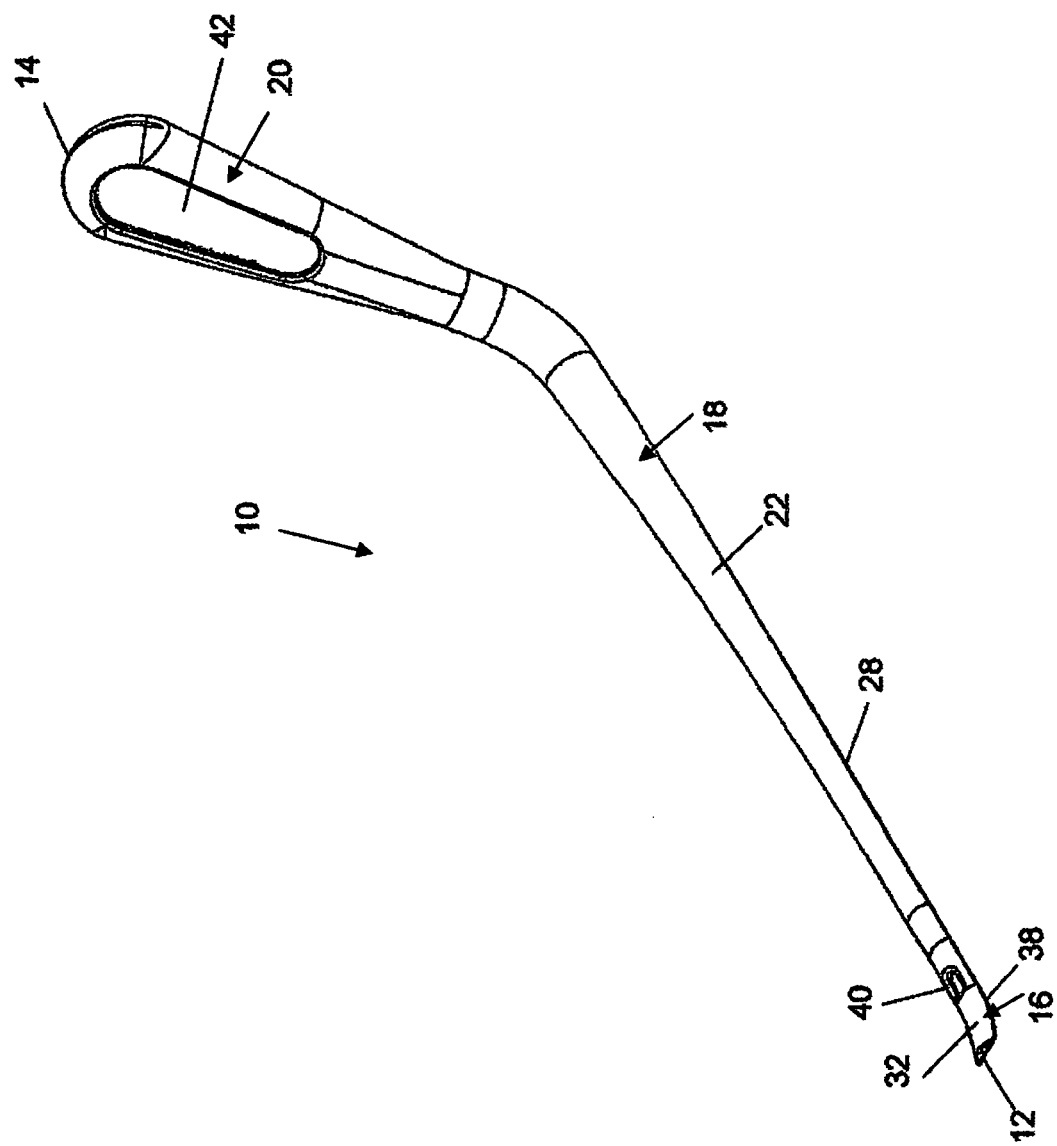
FIG. 4 is a perspective view of the tool of FIG. 1.
Figure 5:
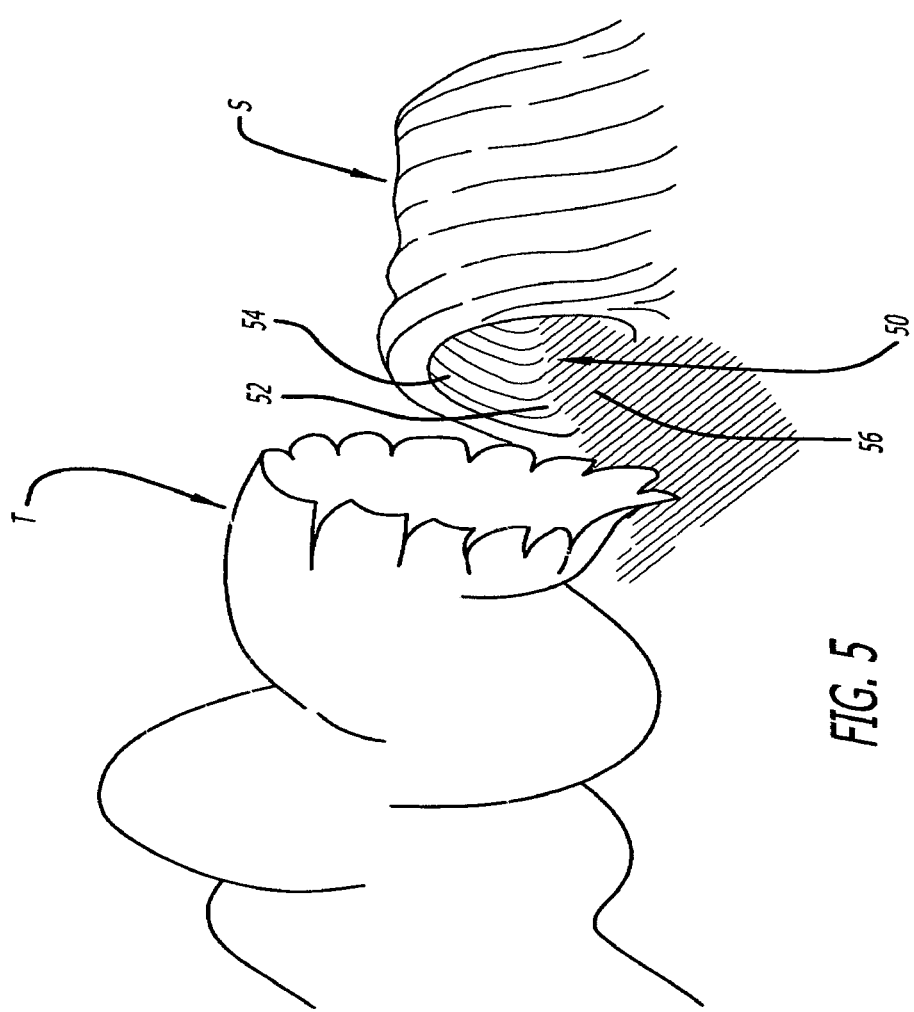
FIG. 5 is a perspective view of a severed flexor tendon adjacent a flexor tendon sheath (or corresponding pulley)
Figure 6:
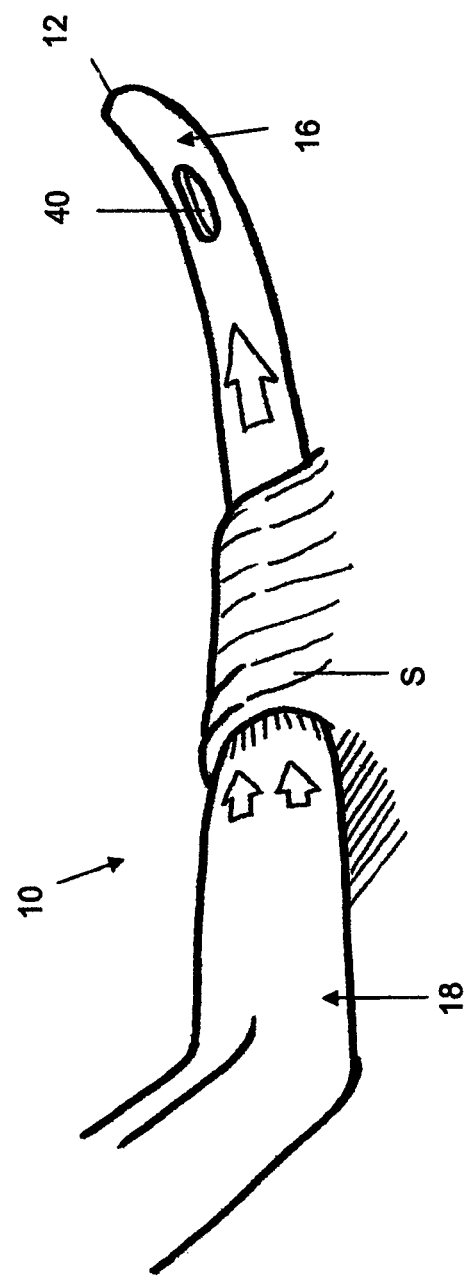
FIG. 6 is a perspective view of the tool of FIG. 1 inserted through a flexor tendon sheath (or corresponding pulley).

FIGS. 1-4 depict one preferred embodiment of a suture retriever-sheath dilator tool according to the present invention. The preferred embodiment of the suture retriever-sheath dilator tool is generally indicated by the numeral 10. As depicted in FIG. 5, a severed flexor tendon T is depicted adjacent a flexor tendon sheath S. Although only one severed flexor tendon T is depicted in FIG. 5, tool 10 can be used in facilitating retrieval and repair both the flexor digitorum superficialis and the flexor digitorum profundis. Tool 10, as depicted in FIG. 6, also manipulates the flexor tendon sheath S and the corresponding pulleys during such retrieval and repair. As discussed below, description of the flexor tendon sheath S also refers to corresponding pulleys thereof.

Tool 10 and components thereof can be elastic, thereby providing tool 10 with flexibility and resiliency. To that end, tool 10 can be made of a single polymeric material such as, for example, polypropylene, or more particularly Santoprene™. The flexibility of tool 10 affords movement thereof within flexor tendon sheath S, while inhibiting potential damage to flexor tendon sheath S due to such movement. Furthermore, the resiliency of tool 10 affords the cross-section of at least a portion thereof to contract and thereafter expand. In doing so, the cross-section of at least a portion of tool 10 can ultimately return to the original uncontracted dimensions thereof. As such, the dimensions of the tool 10 include a degree of memory. As discussed below, under pressure from flexor tendon sheath S that has contracted, at least a portion of tool 10 contracts from a pre-insertion cross-section to a smaller first post-insertion cross-section. Thereafter, at least a portion of tool 10 expands from the first post-insertion cross-section to a larger second post-insertion cross-section to dilate contracted flexor tendon sheath S.

Figure 1:
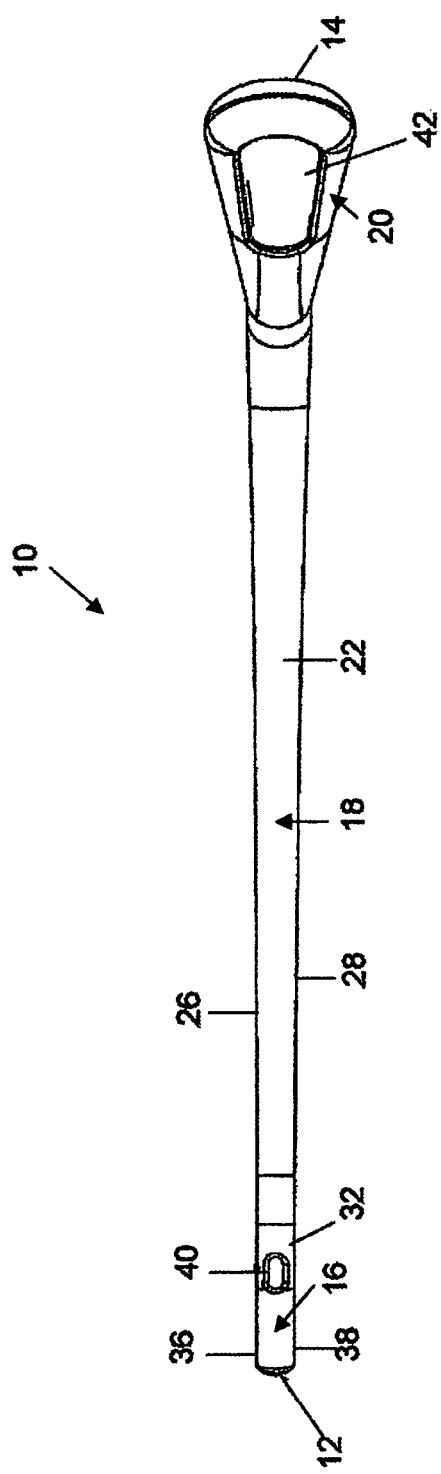
FIG. 1 is a top plan view of one embodiment of a suture retriever-sheath dilator tool according to the present invention.
Figure 2:
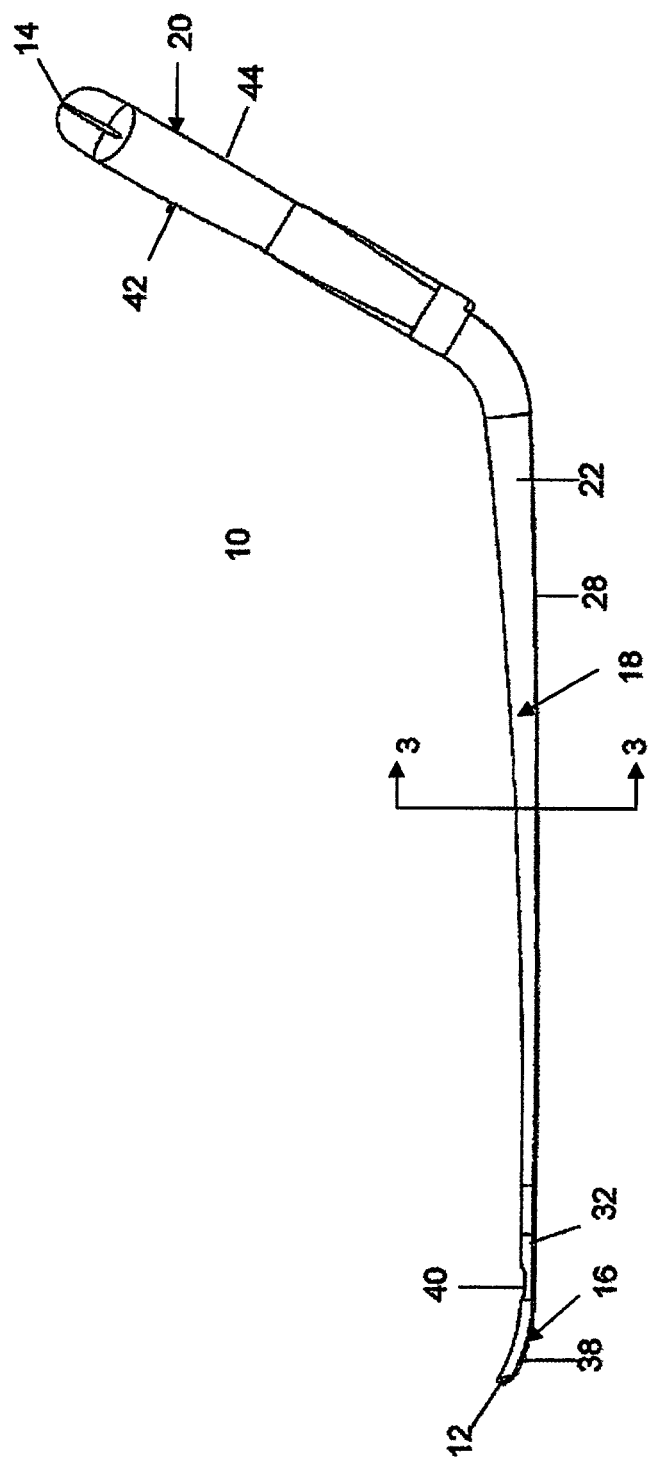
FIG. 2 is a side elevational view of the tool of FIG. 1.

As depicted in FIGS. 1-3, tool 10 includes a distal end 12 and an opposite proximal end 14, and includes a tip portion 16, a shaft portion 18, and a handle portion 20. Shaft portion 18 is positioned between tip portion 16 and handle portion 20. Tip portion 16 extends from distal end 12 to shaft portion 18, and handle portion 20 extends from shaft portion 18 to proximal end 14. During use of tool 10, tip portion 16 and at least a part of shaft portion 18 are passed through flexor tendon sheath S, and handle portion 20 is used to control passage of tip portion 16 and at least a part of shaft portion 18 therethrough. As discussed above, during use of tool 10, the cross-section of at least a portion thereof (such as tip portion 16 and/or shaft portion 18) can contract and thereafter expand. Thus, tool 10 is depicted in FIGS. 1-4 with the original uncontracted dimensions thereof.

The shaft portion 18 includes a length extending between tip portion 16 and handle portion 20, a width perpendicular to the length thereof, and a thickness perpendicular to the length and the width thereof between an upper surface 22 and a lower surface 24. As discussed below, at least one of the thickness and the width of the shaft portion 18 can increase along the length thereof.

The length of shaft portion 18 can range from 1 inch to 4 inches or more, with 2 inches to 3 inches being the preferred range of lengths for repairing severed flexor tendon T. Furthermore, at least a portion of shaft portion 18 can have a curvature along the length thereof. For example, along the length of shaft portion 18, upper surface 22 can have a concave curvature and lower surface 24 can have a convex curvature. The radius of curvature of upper surface 22 of shaft portion 18 along the length thereof preferably ranges from 10 inches to 30 inches, with 15 inches to 25 inches being a more preferred range.

The width of shaft portion 18 extends between lateral edges 26 and 28, and can increase over at least a portion of the length thereof from tip portion 16 to handle portion 20. The increase in the width of shaft portion 18 could be gradual (as depicted in FIG. 1) or be incremented in steps. As depicted in FIG. 1, the width of shaft portion 18 increases from tip portion 16 to handle portion 20 over the entire length thereof. Furthermore, rather than the portion increasing in width being the entire length, the width of shaft portion 18 can increase from tip portion 16 to handle portion 20 over a majority greater than one half of the length, or over a substantial portion less than one half of the length.

The thickness of shaft portion 18 can also increase over at least a portion of the length thereof from tip portion 16 to handle portion 20. The increase in the thickness of shaft portion 18 could be gradual (as depicted in FIG. 2) or be incremented in steps. As depicted in FIG. 2, the thickness of shaft portion 18 increases from tip portion 16 to handle portion 20 over the entire length thereof. Furthermore, rather than the portion increasing in thickness being the entire length, the thickness of shaft portion 18 can increase from tip portion 16 to handle portion 20 over a majority greater than one half of the length, or a substantial portion less than one half of the length.

The flexor tendon sheath S includes an interior 50 having an interior surface 52 with an upper portion 54 and a lower portion 56. During use of tool 10, upper surface 22 likely contacts upper portion 54 of interior surface 52, and lower surface 24 likely contacts lower portion 56 of interior surface 52. Upper surface 22 and lower surface 24 can be flat over at least a portion the length of shaft portion 18. As such, upper surface 22 and lower surface 24 can be flat or generally flat over the entirety of the length of shaft portion 18, a majority greater than one half of the length, or a substantial portion less than one half of the length.

Upper surface 22 and lower surface 24 can alternatively be configured to conform to the anatomy of interior surface 52 of flexor tendon T and/or flexor tendon sheath S. For example, at least a portion of upper surface 22 and at least a portion of lower surface 24 could be provided with a convex curvature or a concave curvature across the width of shaft portion 18 between lateral edges 26 and 38. As depicted in FIG. 4, at least a portion of upper surface 22 can be convex and at least a portion of lower surface 24 can be concave. As such, lower surface 24, for example, could form a recess to receive lower portion 56 of interior surface 52 of flexor tendon sheath S.

The convex configuration of upper surface 22 and the concave configuration of lower surface 24 can be provided over at least a portion of the length of shaft portion 18. As discussed above, the portion of the length of shaft portion 18 can include the entirety of the length of shaft portion 18, a majority greater than one half of the length, or a substantial portion less than one half of the length.

As depicted in FIG. 3, the convex configuration of upper surface 22 and the concave configuration of lower surface 24 are provided at a first cross-section 30 transverse to the length of shaft portion 18. Because the convex configuration of upper surface 22 and the concave configuration of lower surface 24 can be provided over at least a portion of the length of shaft portion 18, shaft portion 18 can include additional cross-sections transverse to the length thereof having the convex configuration of upper surface 22 and the concave configuration of lower surface 24.

Given that the width and the thickness of shaft portion 18 can vary along the length thereof, the sizes of the cross-sections of shaft portion 18 transverse to the length thereof will also vary. For example, the width and the thickness of shaft portion 18, as depicted in FIGS. 1 and 2, increase from tip portion 16 to handle portion 20 along the length of shaft portion 18. Thus, the cross-sectional area of shaft portion 18 can increase from tip portion 16 to handle portion 20 over at least a portion of shaft portion 18. As depicted in FIGS. 1 and 2, the dimensions of a cross-section of shaft portion 18 adjacent tip portion 16 is smaller than the dimensions of a cross-section of shaft portion 18 adjacent handle portion 20. Thus, because first cross-section 30 is provided in the middle of the length of shaft portion 18, the dimensions of first cross-section 30 will be greater than cross-sections of shaft portion 18 closer to tip portion 16 and be less than cross-sections of shaft portion 18 closer to handle portion 20.

As depicted in FIG. 3, upper surface 22 and lower surface 24 intersect with one another along lateral edges 26 and 28 of shaft portion 18. Thus, given the convex configuration of upper surface 22 and the concave configuration of lower surface 24, the radius of curvature of the concave configuration of lower portion 24 is larger than the radius of curvature of the convex configuration of upper portion 22. If, rather than intersecting with one another along lateral edges 26 and 28, upper surface 22 and lower surface 24 were spaced apart from one another, the radius of curvature of the concave configuration of upper surface 22 alternatively could be greater than the radius of curvature of the convex configuration of lower surface 24.

With the original uncontracted dimensions of shaft portion 18, the radius of curvature of the convex configuration of upper portion 22 across the width thereof preferably ranges from 0.03 inches to 0.09 inches, with 0.05 inches to 0.07 inches being a more preferred range. Furthermore, with the original uncontracted dimensions of shaft portion 18, the radius of curvature of the concave configuration of lower portion 24 across the width thereof preferably ranges from 0.05 inches to 0.13 inches, with 0.07 inches to 0.11 inches being a more preferred range.

The tip portion 16 includes a length extending from distal end 12 of tool 10 to shaft portion 18. Furthermore, tip portion 16 includes a width perpendicular to the length thereof, and a thickness perpendicular to the length and the width thereof between an upper surface 32 and a lower surface (not shown). As discussed below, at least one of the thickness and the width of the tip portion 16 can increase along the length thereof. As depicted in FIG. 2, tip portion 16 is curved upwardly. As such, along the length of tip portion 16, upper surface 32 can have a concave curvature and the lower surface can have a convex curvature. The upward curve of tip portion 16 can aid insertion thereof into and through flexor tendon sheath S.

As depicted in FIG. 1, the width of tip portion 16 is no greater than the minimum width of shaft portion 18, and thickness of tip portion 16 is no greater than the minimum thickness of shaft portion 18. Furthermore, the width and the thickness of tip portion 16 can increase over at least a portion of the length from distal end 12 of tool 10 to shaft portion 18. Thus, similarly to shaft portion 18, the cross-sectional area of tip portion 16 can increase over at least a portion of the length from distal end 12 of tool 10 to shaft portion 18. The portion of the length of tip portion 16 can include the entirety of the length, a majority greater than one half of the length, or a substantial portion less than one half of the length. Furthermore, the increase in the width and the thickness of tip portion 16 could be gradual (as depicted in FIGS. 1 and 2) or be incremented in steps.

As depicted in FIG. 2, upper surface 32 and the lower surface of tip portion 16 can be continuous with upper surface 22 and lower surface 24, respectively, of shaft portion 18. Furthermore, upper surface 32 and the lower surface could be provided with a convex curvature or a concave curvature across the width of tip portion 16 between lateral sides 36 and 38 thereof. As such, upper surface 32 can share the convex configuration of upper surface 22 of shaft portion 18, and the lower surface can share the convex configuration of lower surface 24 of shaft portion 18.

The convex configuration of upper surface 32 and the concave configuration of the lower surface can be provided over at least a portion of the length of tip portion 16. With the original uncontracted dimensions of tip portion 16, the radius of curvature of upper surface 32 across the width thereof preferably ranges from 0.03 inches to 0.07 inches. Alternatively, upper surface 32 and the lower surface of tip portion 16 can be flat or generally flat over at least a portion of the length of tip portion 16. The portion of the length of tip portion 16 can include the entirety of the length, a majority greater than one half of the length, or a substantial portion less than one half of the length.

Tip portion 16 also includes a hole 40 to permit a suture and a suture needle to pass therethrough. Alternatively, tip portion 16 can be pierced with the suture needle. For example, tip portion 16 can be configured so that the thickness thereof allows for penetration of the suture needle therethrough. Either way, tip portion 16 can be configured to allow severed flexor tendon T to be attached to tool 10 using the suture and the suture needle.

Handle portion 20 is used in manipulating tool 10. As discussed above, handle portion 20 is to control passage of tip portion 16 and at least a part of shaft portion 18 through flexor tendon sheath S. To that end, handle portion 20 includes gripping surfaces 42 and 44. Furthermore, to aid manipulation of tool 10, handle portion 20 is provided at an angle to shaft portion 18. The angle of handle portion 20 to shaft portion 18 can be obtuse, with 100 to 140 degrees being the preferred range.

As discussed above, interior 50 of flexor tendon sheath S includes interior surface 52 with upper portion 54 and lower portion 56. During use, tool 10 is initially inserted into interior 50 to facilitate dilation of flexor tendon sheath S. As discussed above, one or more of the widths and thicknesses of tip portion 16 and shaft portion 18 can increase in a direction from distal end 12 to proximal end 14 of tool 10.

Due to the absence of flexor tendon T therefrom, flexor tendon sheath S has contracted. Flexor tendon sheath S can be expanded through the insertion (as depicted in FIG. 6) of tip portion 16 and at least a part of shaft portion 18 into interior 50. In doing so, tip portion 16 facilitates insertion of tool 10 into contracted flexor tendon sheath S. Given that the thickness of tip portion 16 is smaller than the thickness of shaft portion 18 and the dimensions of interior 50, tip portion 16 is configured to fit between upper portion 54 and lower portion 56, but not necessarily to contact both. After insertion of tip portion 16, upper surface 22 and lower surface 24 of at least a part of shaft portion 18 are contacted with upper portion 54 and lower portion 56, respectively. Thus, through contact of upper surface 22 with upper portion 54 and contact of lower surface 24 with lower portion 56, at least a part of shaft portion 18 can serve as a wedge against upper portion 54 and lower portion 56 of interior surface 52 to partially dilate contracted flexor tendon sheath S.

Furthermore, under pressure from interior surface 50 of contracted flexor tendon sheath S, the resiliency of tool 10 allows contraction and thereafter expansion. For example, tip portion 16 and/or shaft portion 18 can be capable of such contraction and thereafter expansion. Accordingly, under pressure from contracted flexor tendon sheath S, tip portion 16 and/or shaft portion 18 will contract. Contraction allows tip portion 16 and at least a part of shaft portion 18 to pass through interior 50. Once passage is complete, the resiliency thereof allows tip portion 16 and/or shaft portion 18 to thereafter expand. The expansion of tip portion 16 and/or shaft portion 18 toward the original uncontracted dimensions thereof further dilates contracted flexor tendon sheath S. To afford such dilation, tip portion 16 and/or shaft portion 18 can be left in position within interior 50 to expand toward the original uncontracted dimensions thereof for a preferred range of 20 seconds to 5 minutes, a more preferred range 1 to 4 minutes, and a still more preferred range of 2 to 3 minutes.

During contraction and thereafter expansion of tip portion 16 and/or shaft portion 18, the cross-sections thereof will correspondingly contract and thereafter expand. Thus, under pressure from the contracted flexor tendon sheath S, portions of tip portion 16 and/or shaft portion 18 will contract from pre-insertion cross-sections to smaller first post-insertion cross-sections. The portions of tip portion 16 and/or shaft portion 18 will thereafter expand from the first post-insertion cross-sections to larger second post-insertion cross-sections to dilate contracted flexor tendon sheath S. Dilation of contracted flexor tendon sheath S allows tool 10 to be further inserted therethrough to allow at least a part of shaft portion 18 to further wedge upper portion 54 and lower portion 56 of interior surface 52 apart and thus further dilate. Thus, dilation of contracted flexor tendon sheath S can occur incrementally in two or more controlled iterations.

An indicia can be provided on shaft portion 18 correlated to the thickness and/or width thereof. Thus, a surgeon can measure the size of severed flexor tendon T, and have an indication of the depth shaft portion 18 need be inserted into interior 50 to permit flexor tendon T to pass therethrough.

After insertion of tip portion 16 and at least a part of shaft portion 18 through interior 50, severed flexor tendon T is secured to tip portion 16. As discussed above, hole 40 facilitates attachment of the suture and the suture needle (also attached to severed flexor tendon T) to tip portion 16. Furthermore, tip portion 16 can be pierced with the suture needle to facilitate attachment of the suture and the suture needle (also attached to severed flexor tendon T) thereto. In either instance, severed flexor tendon T can be attached to tip portion 16 at or adjacent distal end 12 of tool 10. Alternatively, given that tip portion 16 is configured to fit between upper portion 54 and lower portion 56, but not necessarily to contact both, severed flexor tendon T can be contacted to upper surface 32 and/or the lower surface to facilitate attachment thereof to tool 10, and still fit within interior 50 during withdrawal of tool 10. Furthermore, depending on the thickness of shaft portion 16 adjacent tip portion 16, severed flexor tendon T can also be attached to or contact upper surface 22 and/or lower surface 24 to facilitate attachment thereof to tool 10. In a preferred embodiment, the severed flexor tendon T contacts and is sutured to the lower surface of the tip, and further may contact lower surface 24 of shaft portion 16.

Once severed flexor tendon T is attached to tip portion 16, severed flexor tendon T can be passed through flexor tendon sheath S. In doing so, tool 10 (and severed flexor tendon T attached thereto) is withdrawn from flexor tendon sheath S. The dilation of flexor tendon sheath S using tool 10 serves to reduce the difficultly of passing severed flexor tendon T therethrough. Finally, once severed flexor tendon T is passed through flexor tendon sheath S to a repair site, severed flexor tendon T can be reattached. An example of a surgical procedure for tendon repair for which the tool of the present invention can be used to complement and improve is taught and described by Gonzalez-Hernandez in U.S. Publication No. 2009/0048616, incorporated by reference herein.

In summary, tool 10, in one preferred embodiment of the invention, facilitates dilation of flexor tendon sheath S, attachment of severed flexor tendon T thereto, passage of severed flexor tendon T through flexor tendon sheath S, and/or reattachment of severed flexor tendon T. Other embodiments of the invention will be apparent to those skilled in the art from consideration of the specification and practice of the invention disclosed herein. Accordingly, it is intended that the specification and examples be considered as exemplary only, with a true scope and spirit of the invention being indicated by the following claims.

What is claimed is:

1. A suture retriever-sheath dilator tool for use in surgery on a tendon of a patient comprising:
    a distal end, a proximal end opposite the distal end, and a length between the distal and proximal ends;
    a shaft having a distal end, a proximal end opposite the distal end, and a length between the distal and proximal ends of the shaft, the shaft being configured to pass at least in part through a tendon sheath, the shaft having a first cross section transverse to the length of the shaft having a convex upper exterior surface configured to contact an inner surface of the tendon sheath, the first cross section of the shaft having a concave lower exterior surface opposite the convex upper exterior surface configured to contact an outer surface of the tendon, the shaft having a thickness perpendicular to the length of the shaft and between the convex upper and concave lower exterior surfaces, the shaft having a width perpendicular to the thickness and the length of the shaft, the shaft increasing in thickness from said distal end of the shaft to said proximal end of the shaft over at least a portion of the length of the shaft;
    a tip extending from the distal end of the shaft for insertion into and through the tendon sheath, the tip being configured to permit a suture in the tendon to be attached to the tip; and
    a handle extending from the proximal end of the shaft.

2. The tool of claim 1, wherein the shaft increases in width from said distal end of the shaft to said proximal end of the shaft over a portion of the length of the shaft.

3. The tool of claim 1, wherein the convex upper exterior surface has a radius and the concave lower exterior surface has a radius, the radius of the concave lower exterior surface being greater than the radius of the convex upper exterior surface.

4. The tool of claim 1, wherein the shaft has a second cross section transverse to the length of the shaft and a third cross section transverse to the length of the shaft, the second cross section being between the first cross section and the third cross section, the first cross section being proximate the distal end of the shaft, the third cross section being proximate the proximal end of the shaft, the second cross section and the third cross section each having a convex upper exterior surface configured to contact the inner surface of the tendon sheath, each of the first, second, and third cross sections having a radius, the radius of the second cross section being larger than the radius of the first cross section, the radius of the third cross section being larger than the radius of the second cross section.

5. The tool of claim 1, wherein the shaft is formed of an elastic flexible material, the shaft having a pre-insertion cross section along a portion of the length of the shaft that is configured to apply pressure to the inner surface of the tendon sheath when the tool is inserted into the sheath, the shaft having a first post-insertion cross section that is smaller than the pre-insertion cross section as a result of the pressure applied to the shaft by the sheath, the shaft having a second post-insertion cross section that is greater than the first post-insertion cross section as a result of the material of the shaft moving toward the shape of the pre-insertion cross section, each of the pre-insertion cross section and the first and second post-insertion cross sections being measured through the same plane perpendicular to the length of the shaft.

6. The tool of claim 5, the shaft having a second pre-insertion cross section along a portion of the length of the shaft that is configured to apply pressure to the inner surface of the tendon sheath when the tool is inserted into the sheath, the second pre-insertion cross section being between the first pre-insertion cross section and the handle, the shaft having another first post-insertion cross section that is smaller than the second pre-insertion cross section as a result of the pressure applied to the shaft by the sheath upon further insertion of the shaft into the sheath, the shaft having another second post-insertion cross section that is greater than the another first post-insertion cross section as a result of the material of the shaft moving toward the shape of the second pre-insertion cross section, each of the second pre-insertion cross section, the another first post-insertion cross section, and another second post-insertion cross section being measured through the same plane perpendicular to the length of the shaft.

7. A suture retriever-sheath dilator tool for use in surgery on a tendon of a patient comprising:
  a distal end, a proximal end opposite the distal end, and a length between the distal and proximal ends;
  a shaft having a distal end, a proximal end opposite the distal end, and a length between the distal and proximal ends of the shaft, the shaft being configured to pass at least in part through a tendon sheath, the shaft having a first cross section transverse to the length of the shaft having a convex upper exterior surface configured to contact an inner surface of the tendon sheath, the first cross section of the shaft having a concave lower exterior surface opposite the convex upper exterior surface configured to contact an outer surface of the tendon, the shaft having a thickness perpendicular to the length of the shaft and between the convex upper and concave lower exterior surfaces, the shaft having a width perpendicular to the thickness and the length of the shaft, the shaft increasing in thickness from said distal end of the shaft to said proximal end of the shaft over at least a portion of the length of the shaft, the shaft being formed of an elastic flexible material, the shaft having a pre-insertion cross section along a portion of the length of the shaft that is configured to apply pressure to the inner surface of the tendon sheath when the tool is inserted into the sheath, the shaft having a first post-insertion cross section that is smaller than the pre-insertion cross section as a result of the pressure applied to the shaft by the sheath, the shaft having a second post-insertion cross section that is greater than the first post-insertion cross section as a result of the material of the shaft moving toward the shape of the pre-insertion cross section, each of the pre-insertion cross section and the first and second post-insertion cross sections being measured through the same plane perpendicular to the length of the shaft, the shaft having a second pre-insertion cross section along a portion of the length of the shaft that is configured to apply pressure to the inner surface of the tendon sheath when the tool is inserted into the sheath, the second pre-insertion cross section being between the first pre-insertion cross section and the handle, the shaft having another first post-insertion cross section that is smaller than the second pre-insertion cross section as a result of the pressure applied to the shaft by the sheath upon further insertion of the shaft into the sheath, the shaft having another second post-insertion cross section that is greater than the another first post-insertion cross section as a result of the material of the shaft moving toward the shape of the second pre-insertion cross section, each of the second pre-insertion cross section, the another first post-insertion cross section, and another second post-insertion cross section being measured through the same plane perpendicular to the length of the shaft;
  a tip extending from the distal end of the shaft for insertion into and through the tendon sheath, the tip being configured to permit a suture in the tendon to be attached to the tip; and
  a handle extending from the proximal end of the shaft.

8. The tool of claim 7, wherein the shaft has a second cross section transverse to the length of the shaft and a third cross section transverse to the length of the shaft, the second cross section being between the first cross section and the third cross section, the first cross section being proximate the distal end of the shaft, the third cross section being proximate the proximal end of the shaft, the second cross section and the third cross section each having a convex upper exterior surface configured to contact the inner surface of the tendon sheath, each of the first, second, and third cross sections having a radius, the radius of the second cross section being larger than the radius of the first cross section, the radius of the third cross section being larger than the radius of the second cross section.

9. A suture retriever tool for use in surgery on a tendon of a patient comprising:
  a distal end, a proximal end opposite the distal end, and a length between the distal and proximal ends;
  a shaft having a distal end, a proximal end opposite the distal end, and a length between the distal and proximal ends of the shaft, the shaft being flexible and configured to pass at least in part through a tendon sheath, the shaft having a first cross section transverse to the length of the shaft having a convex upper exterior surface configured to contact an inner surface of the tendon sheath, the first cross section of the shaft having a concave lower exterior surface opposite the convex upper exterior surface configured to contact an outer surface of the tendon, the shaft having a thickness perpendicular to the length of the shaft and between the convex upper and concave lower exterior surfaces, the shaft having a width perpendicular to the thickness and the length of the shaft, the convex upper exterior surface having a radius and the concave lower exterior surface having a radius, the radius of the concave lower exterior surface being greater than the radius of the convex upper exterior surface wherein the shaft has a second cross section transverse to the length of the shaft and a third cross section transverse to the length of the shaft, the second cross section being between the first cross section and the third cross section, the first cross section being proximate the distal end of the shaft, the third cross section being proximate the proximal end of the shaft, the second cross section and the third cross section each having a convex upper exterior surface configured to contact the inner surface of the tendon sheath, each of the first, second, and third cross sections having a radius, the radius of the second cross section being larger than the radius of the first cross section, the radius of the third cross section being larger than the radius of the second cross section;

a tip extending from the distal end of the shaft for insertion into and through the tendon sheath, the tip having a hole configured to permit a suture needle to pass therethrough; and a handle extending from the proximal end of the shaft, the handle having an upper surface that is at an obtuse angle to the upper surface of the shaft.

10. The tool of claim 9, the shaft having a pre-insertion cross section along a portion of the length of the shaft that is configured to apply pressure to the inner surface of the tendon sheath when the tool is inserted into the sheath, the shaft having a first post-insertion cross section that is smaller than the pre-insertion cross section as a result of the pressure applied to the shaft by the sheath, the shaft having a second post-insertion cross section that is greater than the first post-insertion cross section as a result of the material of the shaft moving toward the shape of the pre-insertion cross section, each of the pre-insertion cross section and the first and second post-insertion cross sections being measured through the same plane perpendicular to the length of the shaft.

11. The tool of claim 10, the shaft having a second pre-insertion cross section along a portion of the length of the shaft that is configured to apply pressure to the inner surface of the tendon sheath when the tool is inserted into the sheath, the second pre-insertion cross section being between the first pre-insertion cross section and the handle, the shaft having another first post-insertion cross section that is smaller than the second pre-insertion cross section as a result of the pressure applied to the shaft by the sheath upon further insertion of the shaft into the sheath, the shaft having another second post-insertion cross section that is greater than the another first post-insertion cross section as a result of the material of the shaft moving toward the shape of the second pre-insertion cross section, each of the second pre-insertion cross section, the another first post-insertion cross section, and another second post-insertion cross section being measured through the same plane perpendicular to the length of the shaft.

* * * * *